United States Patent [19]
Johnston

[11] Patent Number: 5,092,856
[45] Date of Patent: Mar. 3, 1992

[54] VALVE FOR CATHETER RESERVOIR BAG

[76] Inventor: Keith E. Johnston, 14223 Bateau, Cypress, Tex. 77429

[21] Appl. No.: 587,866

[22] Filed: Sep. 24, 1990

[51] Int. Cl.$^5$ ............................................. A61M 5/00
[52] U.S. Cl. ..................................... 604/249; 604/34
[58] Field of Search ................... 604/249, 250, 34, 30, 604/36

[56] References Cited

U.S. PATENT DOCUMENTS 3,044,466  7/1962  Henderson ............................. 604/34
4,702,733  10/1987  Wright et al. ................... 604/250 X

*Primary Examiner*—John D. Yasko
*Attorney, Agent, or Firm*—Neal J. Mosely

[57] ABSTRACT

A drain valve is disclosed which is adapted to be attached to the frame of a wheelchair, bed, or other object for draining a catheter reservoir bag without any part of the reservoir bag contents coming in contact with the valve. The valve has an integral spring-loaded plunger which pinches closed the drain tubing of the reservoir bag. The plunger is connected through a flexible cable to a control device. The valve is normally closed pinching closed the drain tubing, and the reservoir bag is filled through the inlet tubing attached to the patient. When the reservoir bag is to be drained, the control device is activated by the patient to retract the spring-loaded plunger in the valve opening the drain tubing and allowing the reservoir bag to darin. In one embodiment, the control device is a remotely operated hand lever mechanism connected to the cable. In another embodiment, the control device is a solenoid operator connected to the cable.

9 Claims, 1 Drawing Sheet

U.S. Patent    Mar. 3, 1992    5,092,856
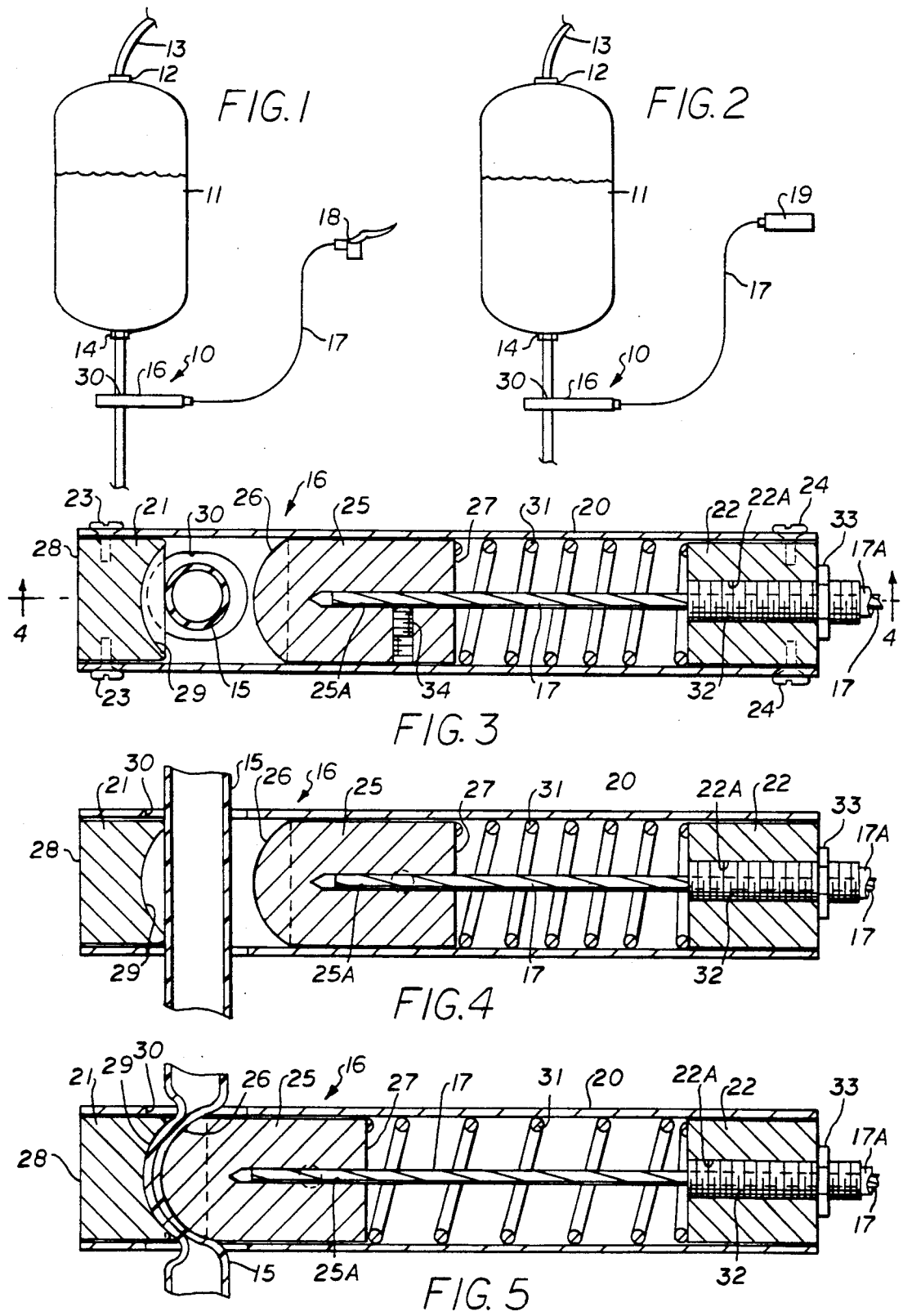

VALVE FOR CATHETER RESERVOIR BAG

BACKGROUND OF THE INVENTION

1. Field of the Invention

This invention relates generally to devices for emptying catheter reservoir bags, and more particularly to a valve for draining a catheter reservoir bag in which none of the parts of the valve come in contact with the reservoir contents.

2. Brief Description of the Prior Art

The prior art contains various and sundry apparatus for human waste handling and disposal. Pertinent references in this area include Stoltz U.S. Pat. No. 559,109; Hinman U.S. Pat. No. 3,415,299; Miller U.S. Pat. No. 3,787,903; and Miller U.S. Pat. No. 3,931,650.

Stoltz U.S. Pat. No. 559,109 discloses a device which is nothing more than a portable commode with a flexible rubber cloth which spreads over the commode to contain odors.

Hinman U.S Pat. No. 3,415,299 discloses a container for collecting urine from a patient in which the container can be emptied from its bottom without contaminating the urine in the container or spilling urine on an operator emptying the container. The device includes an emptying tube having a rotary valve core in the tube passageway to manually open and close the passageway. Thus, the valve is in direct contact with urine.

Miller U.S. Pat. No. 3,787,903 discloses an inconspicuous urine collection shield for fitting underneath and around the sides of an upholstered or cushioned seat of a chair.

Miller U.S. Pat. No. 3,931,650 discloses a urine collection container carried by a person confined to a wheelchair including a rigid drain tube connected above and below a valve mounted on the wheelchair. The valve is operated by a hand lever or solenoid. However, the contents of the reservoir bag are in direct contact with the valve interior components when the bag is drained. Thus, the valve would require frequent cleaning and maintenance.

The present invention is distinguished over the prior art in general, and these patents in particular, by a drain valve which is adapted to be attached to the frame of a wheelchair, bed, or other object for draining a catheter reservoir bag without any part of the reservoir bag contents coming in contact with the valve. The valve has an integral spring-loaded plunger which pinches closed the drain tubing of the reservoir bag. The plunger is connected through a flexible cable to a control device. The valve is normally closed pinching closed the drain tubing, and the reservoir bag is filled through the inlet tubing attached to the patient. When the reservoir bag is to be drained, the control device is activated by the patient to retract the spring-loaded plunger in the valve opening the drain tubing and allowing the reservoir bag to drain. In one embodiment, the control device is a remotely operated hand lever mechanism connected to the cable. In another embodiment, the control device is a solenoid operator connected to the cable.

SUMMARY OF THE INVENTION

It is therefore an object of the present invention to provide a valve for draining a catheter reservoir bag without any part of the valve apparatus coming in direct contact with the reservoir contents.

It is another object of this invention to provide a valve for draining a catheter reservoir bag which is adapted to be attached to the frame of a wheelchair, bed frame or to the patient's leg.

Another object of this invention is to provide a valve for draining a catheter reservoir bag with a valve mechanism which pinches closed the outlet tubing on the reservoir bag.

Another object of this invention is to provide a valve for draining a catheter reservoir bag which has an integral spring-loaded plunger which pushes against the outlet tubing for closing the tubing.

Another object of this invention is to provide a valve for draining a catheter reservoir bag which has an integral spring-loaded plunger connected through a flexible cable operator to a control device remote from the valve.

A further object of this invention is to provide a valve for draining a catheter reservoir bag which has an integral spring-loaded plunger connected through a flexible cable operator to a hand lever operator mechanism.

A still further object of this invention is to provide a valve for draining a catheter reservoir bag which has an integral spring-loaded plunger connected through a flexible cable operator to a solenoid operator remote from the valve.

Other objects of the invention will become apparent from time to time throughout the specification and claims as hereinafter related.

The above noted objects and other objects of the invention are accomplished by a drain valve which is adapted to be attached to the frame of a wheelchair, bed, or other object for draining a catheter reservoir bag without any part of the reservoir bag contents coming in contact with the valve. The valve has an integral spring-loaded plunger which pinches closed the draint tubing of the reservoir bag. The plunger is connected through a flexible cable to a control device. The valve is normally closed pinching closed the drain tubing, and the reservoir bag is filled through the inlet tubing attached to the patient. When the reservoir bag is to be drained, the control device is activated by the patient to retract the spring-loaded plunger in the valve opening the drain tubing and allowing the reservoir bag to drain. In one embodiment, the control device is a remotely operated hand lever mechanism connected to the cable. In another embodiment, the control device is a solenoid operator connected to the cable.

BRIEF DESCRIPTION OF THE DRAWINGS

FIG. 1 is a schematic side elevation of the valve apparatus for draining a catheter reservoir bag in accordance with the present invention which has a hand lever control.

FIG. 2 is a schematic side elevation of the valve apparatus for draining a catheter reservoir bag in accordance with the present invention which has a solenoid control.

FIG. 3 is a cross-section view of the valve of the present invention shown with the plunger retracted.

FIG. 4 is a cross-section view of the valve of the present invention taken on the section line 4—4 of FIG. 3 showing the plunger retracted.

FIG. 5 is a cross-section view of the valve of the present invention similar to FIG. 4 showing the plunger in the extended, or closed position.

DESCRIPTION OF THE PREFERRED EMBODIMENT

Referring to the drawings by numerals of reference, there is shown in FIG. 1, a preferred embodiment of the automatic valve apparatus 10 for draining a catheter reservoir bag which has a hand lever control, and in FIG. 2, an embodiment of the apparatus 10 which has a solenoid control.

The reservoir bag 11 has an inlet 12 and inlet tubing 13 extending to a catheter. An outlet 14 from bag 11 is connected by flexible tubing 15 for draining the contents of the bag. The tubing 15 passes through a valve 16 in accordance with the present invention. The valve 16 is connected by flexible cable 17 to a remote operator for opening or closing the valve. In FIG. 1, flexible cable 17 has a manual operator, or hand lever, 18 similar to those used on bicycle caliper hand brakes. As shown in FIG. 2, a solenoid operator 19 may alternatively be connected to the cable 17 for remote operation of the valve.

Referring now to FIGS. 3, 4 and 5, there are shown cross-section views of the drain valve 16 of FIG. 1. Valve 16 comprises a tubular outer housing 20 having a base cap 21 at one end, and an end cap 22 at the other end. The caps 21 and 22 ar attached to the outer housing 20 by attachment screws 23 and 24. End cap 22 has a longitudinal threaded aperture 22A.

A valve plunger 25 is positioned for sliding movement in housing 20. Plunger 25 is cylindrical in shape with a forward end 26 of spherical curvature, a flat rear end 27, and has a longitudinal bore 25A extending inwardly from the end 27. Base cap 21 is cylindrical in shape and has a flat end 28 and a spherically concave end 29 mating with the spherical end 26 of plunger 25 when the plunger is fully extended. Openings 30 in housing 20 permit insertion of reservoir bag drain tube 15 therethrough. Other openings may be provided in housing 20 to permit insertion of fingers or tools for servicing the valve.

A compression spring 31 is positioned between end cap 22 and the flat end 27 of the plunger 25 to urge the valve plunger toward a closed position with spherical end 26 approaching (touching when no drain tube is present) spherically concave end 29 of base cap 28. Flexible cable 17 has a flexible outer sheath 17A in which the cable 17 slides. The end of cable sheath 17A is received in a tubular cable receiving adjustment member 32 having external threads. The adjustment member 32 is threadedly secured in the threaded aperture 22A of end cap 22 with a portion extending outwardly therefrom. The interior of the adjustment member 32 is figured to engage and secure the cable sheath 17A. A locknut 33 is received on the extended end of member 32 for adjusting the stroke of the plunger 25 relative to the end of sheath 17A. Cable 17 extends inwardly beyond the end of the adjustment member 32, through spring 31, and into the longitudinal bore 25A in plunger 25 and is secured in place by set screw 34 installed through the plunger side wall.

In FIGS. 3-4, the valve 16 is shown with the flexible outlet tubing 15 extending through openings 30 in valve housing 20 between the end 26 of valve plunger 25 and spherically concave end 29 of base cap 28. The plunger 25 is retracted and flexible tube 15 is open for drainage of liquid from reservoir bag 11. In FIG. 5, the plunger 25 is shown extended to compress tube 15 between plunger end 26 and concave end 29 to close or pinch-off the tube, thus preventing the passage of the contents of the reservoir bag 11.

OPERATION

The operation of the present invention should be obvious from the detailed description of the preferred embodiment, but will be stated herein for clarity.

With the outlet tubing 15 pinched closed (FIG. 5), the empty reservoir bag 11 is allowed to fill through the inlet tubing 13 attached to the patient. When the level in the reservoir bag 11 rises to the point that it must be drained, the patient opens the outlet tubing 15 for draining. This is done by operating the control device lever 18 or solenoid 19 to pull cable 17 and plunger 25 to an open or retracted position. In the embodiment using a hand lever, control device 18, the plunger is retracted manually. In the solenoid operated embodiment, the plunger is retracted by solenoid operator 19 to pull the cable. The solenoid 19 would be connected through a switch to an electrical source using conventional wiring hook up (not shown).

The valve 16 is preferably connected to the footrest portion or the frame of a wheelchair, or to a bed frame, but may be connected to any object in close proximity to the drain tube 15. The control device 18 or 19 for remote operation is positioned for easy access by the patient.

While this invention has been described fully and completely with special emphasis upon a preferred embodiment, it should be understood that, within the scope of the appended claims, the invention may be practiced otherwise than as specifically described herein.

I claim:

1. A catheter assembly and control valve therefor comprising:
    a reservoir bas having an inlet end and a single flexible drain tube for draining the contents thereof,
    a catheter tube having one end for insertion into a human body orifice and its other end connected to said bag inlet end,
    a drain valve connected to said single bag drain tube for controlling flow of the contents from said bag,
    said valve being connected with said single bag drain tube such that no part of the bag contents contact said valve,
    said valve having a housing with openings through which said single flexible drain tube extends,
    a valve plunger slidably positioned in said valve housing and operable to move longitudinally therein,
    a spring positioned in said valve housing to urge said valve plunger toward an extended position to pinch closed said single drain tube for filling said reservoir bag,
    control means operatively connected to said valve plunger for moving said plunger between a normally extended position pinching said single drain tube closed and a retracted position opening said drain tube and allowing the contents of said reservoir bag to drain therethrough, and
    said bag and valve being adapted to be secured adjacent to the catheterized body.

2. A catheter assembly and control valve according to claim 1 in which;
    said control means comprises a lever mechanism remote from said valve housing, and
    a length flexible cable having one end connected to said plunger and its other end connected to said lever mechanism, whereby operation of said lever mechanism retracts said plunger for opening said single drain tube.

3. A catheter assembly and control valve according to claim 1 in which;
said drain valve housing comprises a tubular member,
a base cap enclosing one end of said tubular member,
an end cap enclosing the opposite end of said tubular member,
apertures in the side wall of said tubular member axially aligned for receiving said single drain tube therethrough and disposed to position said single drain tube between said base cap and said valve plunger.

4. A catheter assembly and control valve according to claim 3 in which
said end cap has cable connection means at one end for receiving and adjustably securing one end of a flexible cable thereto.

5. A catheter assembly and control valve according to claim 3 in which
said base cap and said valve plunger having opposite facing ends configured to cooperatively engage said single drain tube such that it is maintained pinched closed when said valve plunger is in said extended position.

6. A catheter assembly and control valve according to claim 5 in which;
said base cap and said valve plunger opposite facing ends comprise congruous curved surfaces, whereby
a portion of said single drain tube is received therebetween and is pinched closed when said valve plunger is moved to said extended position.

7. A catheter assembly and control valve according to claim 6 in which
said valve plunger has a convex spherical forward end engageable with said single drain tube.

8. A catheter assembly and control valve according to claim 6 in which
said base cap has a concave spherical end engageable with said single drain tube.

9. A catheter assembly and control valve according to claim 6 in which;
said valve plunger has a convex spherical forward end engageable with said drain tube, and
said base cap has a concave spherical end engageable with said single drain tube.

* * * * *